United States Patent
Raichle et al.

(10) Patent No.: US 8,895,783 B2
(45) Date of Patent: Nov. 25, 2014

(54) MONITORING OF THE STOICHIOMETRIC RATIO IN THE REACTION OF NITROAROMATICS WITH HYDROGEN

(71) Applicant: BASF SE, Ludwigshafen (DE)

(72) Inventors: Andreas Raichle, Ludwigshafen (DE); Stefanie Haase, Bretnig-Hauswalde (DE); Holgar Braunsberg, Senftenberg (DE); Johannes Buettner, Ruhland (DE); Ulrich Penzel, Tettau (DE); Samuel Neto, Brussels (BE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/759,466

(22) Filed: Feb. 5, 2013

(65) Prior Publication Data
US 2013/0211141 A1    Aug. 15, 2013

Related U.S. Application Data

(60) Provisional application No. 61/595,706, filed on Feb. 7, 2012.

(51) Int. Cl.
C07C 209/00 (2006.01)
C07C 209/36 (2006.01)

(52) U.S. Cl.
CPC .................... *C07C 209/36* (2013.01)
USPC ........................................ 564/420

(58) Field of Classification Search
CPC .................................................. C07C 209/36
See application file for complete search history.

(56) References Cited

U.S. PATENT DOCUMENTS

| | | | |
|---|---|---|---|
| 6,677,271 B1 | 1/2004 | Birke et al. | |
| 6,680,280 B1 | 1/2004 | Birke et al. | |
| 6,894,193 B2 * | 5/2005 | Zehner et al. | 564/420 |
| 2011/0284391 A1 | 11/2011 | Fritz et al. | |
| 2011/0295039 A1 | 12/2011 | Raichle et al. | |

(Continued)

FOREIGN PATENT DOCUMENTS

| | | |
|---|---|---|
| EP | 1 161 297 B1 | 10/2003 |
| EP | 1 165 231 B1 | 10/2003 |

(Continued)

OTHER PUBLICATIONS

U.S. Appl. No. 13/569,806, filed Aug. 8, 2012, Petra Deckert, et al.

(Continued)

*Primary Examiner* — Clinton Brooks
(74) *Attorney, Agent, or Firm* — Oblon, Spivak, McClelland, Maier & Neustadt, L.L.P.

(57) ABSTRACT

The present invention relates to a continuous process for preparing at least one aromatic amine by hydrogenation of at least one nitroaromatic by means of hydrogen, where a liquid phase comprising at least the aromatic amine and a gas phase comprising at least hydrogen are present, in the presence of a catalyst suspended in the liquid phase at a temperature of from 50 to 250° C. and a pressure of from 5 to 50 bar, wherein the pressure in the reactor is kept essentially constant by continuous adaptation of the amount of hydrogen fed to the reactor, the total amount of hydrogen fed to the reactor is monitored and the introduction of the at least one nitroaromatic is interrupted if the hydrogen uptake in the reactor is not at least 50 mol % of the amount of hydrogen required for stoichiometric reaction of the at least one nitroaromatic to form the at least one aromatic amine.

15 Claims, 5 Drawing Sheets

(56) References Cited

U.S. PATENT DOCUMENTS

| | | |
|---|---|---|
| 2012/0197047 A1 | 8/2012 | Allardt et al. |
| 2012/0205308 A1 | 8/2012 | Leschinski et al. |
| 2012/0215029 A1 | 8/2012 | Haase et al. |
| 2012/0238779 A1 | 9/2012 | Waters et al. |

FOREIGN PATENT DOCUMENTS

| | | |
|---|---|---|
| WO | 00/35852 | 6/2000 |
| WO | 02/062729 A2 | 8/2002 |
| WO | 03/068724 A1 | 8/2003 |
| WO | 2011/144481 A1 | 11/2011 |

OTHER PUBLICATIONS

U.S. Appl. No. 13/567,265, filed Aug. 6, 2012, Julia Leschinski, et al.

U.S. Appl. No. 14/147,805, filed Jan. 6, 2014, Bey, et al.

U.S. Appl. No. 14/147,823, filed Jan. 6, 2014, Bey, et al.

* cited by examiner

MONITORING OF THE STOICHIOMETRIC RATIO IN THE REACTION OF NITROAROMATICS WITH HYDROGEN

CROSS-REFERENCE TO RELATED APPLICATIONS

This application is based upon and claims the benefit of priority to U.S. provisional application No. 61/595,706, which was filed on Feb. 7, 2012.

BACKGROUND OF THE INVENTION

The present invention relates to a continuous process for preparing at least one aromatic amine by hydrogenation of at least one nitroaromatic by means of hydrogen, where a liquid phase comprising at least the aromatic amine and a gas phase comprising at least hydrogen are present, in the presence of a catalyst suspended in the liquid phase at a temperature of from 50 to 250° C. and a pressure of from 5 to 50 bar, wherein the pressure in the reactor is kept essentially constant by continuous adaptation of the amount of hydrogen fed to the reactor, the total amount of hydrogen fed to the reactor is monitored and the introduction of the at least one nitroaromatic is interrupted if the hydrogen uptake in the reactor is not at least 50 mol %, preferably at least 70 mol %, particularly preferably at least 90 mol %, very particularly preferably at least 95 mol %, in particular at least 98 mol %, of the amount of hydrogen required for stoichiometric reaction of the at least one nitroaromatic to form the at least one aromatic amine.

Processes for preparing aromatic amines by hydrogenation of the corresponding nitroaromatics are known from the prior art.

WO 02/062729 A2 discloses a process for the hydrogenation of liquid, organic compounds, in particular nitroaromatic compounds, to the corresponding aromatic amine compounds. In a specific embodiment of this process, it is disclosed that a particular pressure is maintained by introduction of hydrogen into the reactor. Furthermore, it is disclosed that the amount of offgas from the reactor in which the reaction mentioned takes place is regulated so that the purity of the discharged hydrogen after removal of the water vapor by condensation is only 90% by volume.

WO 00/35852 likewise discloses a process for producing aromatic amines by reaction of the corresponding nitroaromatic compounds. This document, too, gives no indication of how damage to the catalyst used can be avoided.

The international patent application PCT/EP2011/057427 describes a process for the continuous preparation of toluenediamine by liquid-phase hydrogenation of dinitrotoluene by means of hydrogen in the presence of a suspended, nickel-comprising catalyst in a reactor having a product separation unit downstream of the reactor to give a product output from the reactor comprising a liquid phase comprising toluenediamine and dinitrotoluene in which the nickel-comprising catalyst is suspended, where the concentration of dinitrotoluene in the liquid phase of the product output from the reactor in the region between the reactor and the downstream product separation unit is set to a value in the range from 1 to 200 ppm by weight, based on the total weight of the liquid phase of the product output from the reactor.

The documents of the prior art cited do not give any indication that, in a process for preparing aromatic amines from the corresponding nitroaromatics, the amount of hydrogen should be monitored and when the conversion is too low at constant pressure, the introduction of corresponding nitroaromatic compounds should be stopped in order to avoid damage to the catalyst. Furthermore, the processes known from the prior art are capable of improvement in respect of the speed of detection of a malfunction and the reaction to this malfunction.

In the light of the abovementioned prior art, it is therefore an object of the present invention to provide a continuous process for preparing aromatic amines by catalytic hydrogenation of the corresponding nitroaromatics, by means of which the desired products can be obtained in high purity and yield. A further object is to provide a process by means of which it is possible to operate appropriately even in the case of minor malfunctions in the reaction in order to be able to efficiently avoid damage to the catalyst used. For this purpose, it is necessary for a malfunction occurring in the reaction to be detected as quickly as possible. Furthermore, a process which makes the starting/nonstarting of the catalytic hydrogenation of nitroaromatics to aromatic amines visible should be provided. Furthermore, it is an object of the present invention to provide a corresponding process by means of which accumulation of unreacted nitroaromatic compounds, for example dinitrotoluene (DNT), in the reactor is avoided in order to be able to avoid a potential explosion risk.

BRIEF SUMMARY OF THE INVENTION

These objects are achieved by the continuous process of the invention for preparing at least one aromatic amine by hydrogenation of at least one nitroaromatic by means of hydrogen, where a liquid phase comprising at least the aromatic amine and a gas phase comprising at least hydrogen are present, in the presence of a catalyst suspended in the liquid phase at a temperature of from 50 to 250° C. and a pressure of from 5 to 50 bar, wherein the pressure in the reactor is kept essentially constant by continuous adaptation of the amount of hydrogen fed to the reactor, the total amount of hydrogen fed to the reactor is monitored and the introduction of the at least one nitroaromatic is interrupted if the hydrogen uptake in the reactor is not at least 50 mol %, preferably at least 70 mol %, particularly preferably at least 90 mol %, very particularly preferably at least 95 mol %, in particular at least 98 mol %, of the amount of hydrogen required for stoichiometric reaction of the at least one nitroaromatic to form the at least one aromatic amine.

BACKGROUND OF THE INVENTION

Figure 1:
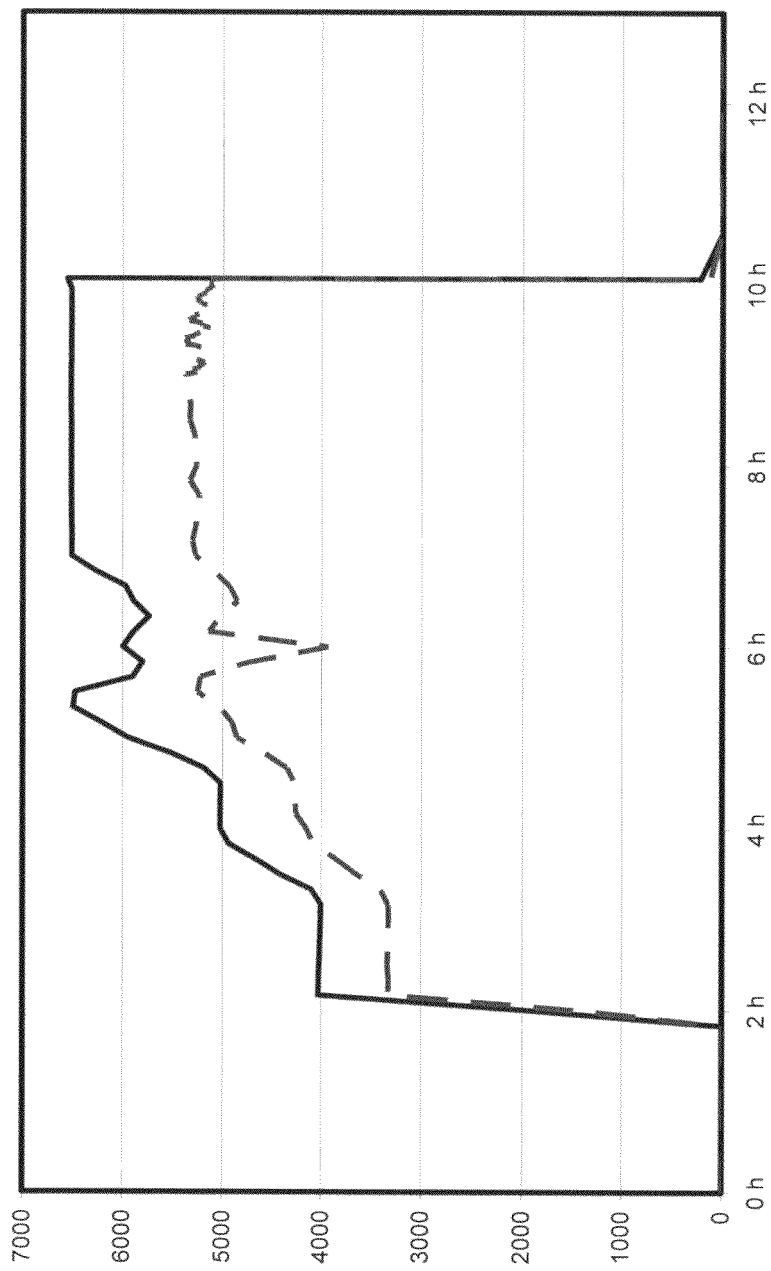
FIG. 1 shows the amount of DNT used (solid line, in kg/h) and amount of hydrogen introduced (broken line, in standard m$^3$/h) versus time in hours for example 1.

In the process of the invention, the pressure in the reactor is kept essentially constant by continuous adaptation of the amount of hydrogen fed to the reactor, the total amount of hydrogen fed to the reactor is monitored and the introduction of the at least one nitroaromatic is interrupted if the hydrogen uptake in the reactor is not at least 50 mol %, preferably at least 70 mol %, particularly preferably at least 90 mol %, very particularly preferably at least 95 mol %, in particular at least 98 mol %, of the amount of hydrogen required for stoichiometric reaction of the at least one nitroaromatic to form the at least one aromatic amine.

Damage to the catalyst used by an excessively high concentration of nitroaromatics in the reactor can be avoided by the process of the invention. Furthermore, the quick interruption of the introduction of nitroaromatics so that an excessively high nitroaromatics concentration cannot occur in the reactor allows a potential explosion risk to be avoided.

The process of the invention is carried out continuously.

According to the invention, "hydrogen uptake" is the total amount of hydrogen introduced into the reactor minus the amount of hydrogen discharged. In a preferred embodiment, the amount of hydrogen discharged is so small that it can to a first approximation be disregarded. The monitoring according to the invention of the hydrogen uptake provides a very rapid method of detecting starting/nonstarting or an undesired slowing ("cessation") of the catalytic hydrogenation of nitroaromatics to aromatic amines and the interruption according to the invention of the introduction of the nitroaromatics provides a rapid method of avoiding catalyst deactivation in the case of nonstarting of the reaction, e.g. due to the amount of catalyst being too small or a catalyst which is too inactive.

In the process of the invention, the pressure in the reactor is kept essentially constant, for example by continuous adaptation of the amount of hydrogen introduced into the reactor. For the purposes of the present invention, "essentially constant" means that the pressure in the reactor fluctuates by not more than 10%, preferably not more than 5%, preferably not more than 3%, above or below the desired reactor pressure.

Keeping the pressure in the reactor essentially constant according to the invention can be successfully achieved, for example, by means of a PID (proportional-integral-differential) regulator programmed in the process control system (PCS).

To be able to determine the hydrogen uptake in the reaction according to the invention of nitroaromatics with hydrogen, the total amount of hydrogen introduced into the reactor is monitored, preferably continuously.

In a further preferred embodiment, the amount and content of hydrogen in the stream discharged is monitored, preferably continuously. The amount of hydrogen discharged is the product of the total amount of offgas discharged and the hydrogen content. Particular preference is therefore given to measuring the hydrogen content in the offgas stream.

In a particularly preferred embodiment, the total amount of hydrogen introduced into the reactor and the amount of hydrogen discharged are monitored, preferably both continuously. Since, according to the invention, the introduction of hydrogen can occur at various places in the reactor, "total amount of hydrogen introduced" preferably means, according to the invention, the sum of all amounts of hydrogen introduced.

According to the invention, the hydrogen used preferably has a purity of >99% by volume, preferably 99.9-99.99% by volume. It is also possible to use hydrogen which can comprise inert constituents, for example noble gases and/or nitrogen, for example in an amount of from 500 to 2000 ppm of nitrogen or argon, see, for example, WO 02/062729 A2. Preference is given to using hydrogen which contains particularly little mercury, preferably less than 30 µg/standard m$^3$, particularly preferably less than 20 µg/standard m$^3$ and very particularly preferably less than 2 µg/standard m$^3$. Any impurities present in the hydrogen used are, according to the invention, preferably taken into account in the determination of the hydrogen uptake. Very particular preference is given to hydrogen comprising at least 99.9% by volume of H$_2$, not more than 20 ppm by volume of CO, preferably less than 10, particularly preferably less than 1, ppm by volume of CO, not more than 2000 ppm by volume of nitrogen, preferably less than 100, particularly preferably 10-30, ppm by volume of nitrogen, not more than 2000 ppm by volume of argon, preferably less than 200, particularly preferably less than 40, ppm by volume of argon, not more than 25 ppm by volume of methane, preferably less than 10, particularly preferably less than 1, ppm by volume of methane, not more than 50 ppm by volume of oxygen, preferably less than 30, particularly preferably less than 5, ppm by volume of oxygen, and not more than 6000 ppm by volume of water, preferably less than 2500, particularly preferably less than 1100, ppm by volume of water.

According to the invention, in the case of a hydrogen purity of greater than 99%, only this is measured. At a hydrogen purity of less than or equal to 99%, this is measured and the introduction of hydrogen is adjusted accordingly or the hydrogen uptake is determined accordingly.

In a preferred embodiment of the process according to the invention, the hydrogen uptake in the reactor corresponding to the stoichiometric reaction of the at least one nitroaromatic is reached not more than 5 minutes, preferably not more than 3 minutes, after commencement of the introduction of the nitroaromatic.

The present invention therefore preferably provides the process of the invention in which the hydrogen uptake in the reactor corresponding to the stoichiometric reaction of the at least one nitroaromatic is reached not more than 5 minutes, preferably not more than 3 minutes, after the commencement of the introduction of the nitroaromatic.

The interruption of the introduction of the at least one nitroaromatic, i.e. shutdown of the reactor, can, according to the invention, be effected by all methods known to those skilled in the art. For example, the interruption of the introduction of the nitroaromatic can be carried out manually, for example by the personnel monitoring the plant, or automatically, for example by switching in the PCS or hard-wired. According to the invention, an interruption is preferably effected when the abovementioned conditions prevail, i.e. when the hydrogen uptake goes below a defined value or preferably when the ratio of hydrogen uptake and the amount required for the stoichiometric reaction of the nitroaromatic to form the aromatic amine goes below a defined value for a particular time, or when the amount of hydrogen introduced goes below a minimum value.

According to the invention, preference is given to the introduction of the at least one nitroaromatic being interrupted as quickly as possible when the hydrogen uptake goes below the values according to the invention. In case of manual interruption, the reaction time is, for example, from 1 to 2 minutes. In the case of automatic interruption, the reaction time is, for example, in the second or millisecond range.

According to the invention, the introduction of the at least one nitroaromatic is interrupted, for example, after less than 2 minutes, preferably after less than 1 minute, particularly preferably after less than 30 seconds, very particularly preferably after less than 5 seconds, in each case determined from the point in time at which the hydrogen uptake goes below the values according to the invention.

To be able to compensate any fluctuations in measured values which may occur, preference is also given to waiting for a short time, for example from 5 to 30 seconds, after detection of the hydrogen uptake going below the values according to the invention before interrupting the introduction of the at least one nitroaromatic.

According to the invention, the monitoring of the hydrogen uptake can be carried out during start-up of the reaction and during the reaction, which is carried out continuously.

In a preferred embodiment of the process of the invention, the introduction of the at least one nitroaromatic is not interrupted during start-up of the reaction even when the hydrogen uptake goes below the values according to the invention. In this embodiment, the interruption of the introduction of the at least one nitroaromatic when the hydrogen uptake goes below the values according to the invention is carried out, for example, only after 5 minutes, preferably after 4 minutes, particularly preferably after 3 minutes, in each case after commencement of start-up of the reaction. For this purpose, for example, the automatic switching is manually overridden during start-up. This preferably goes over automatically into the normal state after a defined time, i.e. interruption of the introduction of the at least one nitroaromatic after, for example, less than 2 minutes, preferably after less than 1 minute, particularly preferably after less than 30 seconds, very particularly preferably after less than 5 seconds.

In a further preferred embodiment, the introduction of the at least one nitroaromatic is not commenced with the total amount, i.e. 100 mol %, introduced during normal operation.

The introduction of the at least one nitroaromatic is preferably commenced with from 10 to 90%, particularly preferably from 20 to 80%, very particularly preferably from 30 to 70 mol %, of the amount of nitroaromatic introduced in normal operation.

The present invention therefore also provides the process of the invention in which the introduction of the at least one nitroaromatic is commenced with from 10 to 90 mol %, preferably from 20 to 80 mol %, particularly preferably from 30 to 70 mol %, of the amount of nitroaromatic introduced in normal operation.

During the reaction, the amount of at least one nitroaromatic introduced at the beginning, which according to the invention is preferably less than 100 mol % of the amount introduced in normal operation, is increased to the amount introduced in normal operation, i.e. 100 mol %. This increase can, according to the invention, be effected by all methods known to those skilled in the art.

The present invention therefore preferably provides the process of the invention in which the amount of nitroaromatic is increased stepwise or continuously during the hydrogenation.

The preferred increase according to the invention can be carried out stepwise, for example manually or programmed in a chain of steps in the PCS, or continuously via a ramp programmed in the PCS.

In a preferred embodiment of the process of the invention, the amount of at least one nitroaromatic introduced in normal operation is reached by stepwise or continuous increase after from 0.5 to 120 hours, preferably from 4 to 72 hours, particularly preferably from 8 to 48 hours and very particularly preferably from 12 to 24 hours, after start-up of the process.

The present invention therefore preferably provides the process of the invention in which the amount of at least one nitroaromatic introduced continuously in normal operation is reached by stepwise or continuous increase after from 0.5 to 120 hours after start-up of the process.

In the process of the invention, the concentrations of nitro compounds are preferably set to from 1 to 200 ppm.

The present invention therefore preferably provides the process of the invention in which the concentrations of nitro compounds are set to from 1 to 200 ppm.

The process of the invention for the hydrogenation of at least one nitroaromatic to at least one aromatic amine can preferably be carried out in any solvent which appears suitable to a person skilled in the art. Examples of suitable solvents are selected from the group consisting of water, organic solvents, in particular polar organic solvents such as alcohols, for example methanol, ethanol, propanol, n-butanol or isobutanol, at least one aromatic amine which is formed during the reaction according to the invention and mixtures thereof. According to the invention, ketones, esters or aldehydes are less preferred as solvents.

The present invention therefore preferably provides the process of the invention in which a solvent which is preferably present is selected from the group consisting of water, organic solvents, in particular polar organic solvents such as alcohols, for example methanol, ethanol, propanol, n-butanol or isobutanol, at least one aromatic amine which is formed during the reaction according to the invention and mixtures thereof.

According to the invention, the liquid phase in the reactor before start-up comprises at least one of the abovementioned solvents. In a preferred embodiment, the liquid phase in the reactor before start-up comprises essentially only water, preferably water and an organic solvent, for example a solvent selected from the group consisting of methanol, ethanol, propanol, n-butanol, isobutanol and mixtures thereof, or particularly preferably water and an organic solvent and/or from 1 to 90% by weight, preferably from 10 to 70% by weight, of the at least one aromatic amine formed during the reaction according to the invention.

The present invention therefore preferably provides the process of the invention in which the liquid phase comprises a solvent selected from the group consisting of water, organic solvents, in particular polar organic solvents such as alcohols, for example methanol, ethanol, propanol, n-butanol or isobutanol, at least one aromatic amine formed during the reaction according to the invention and mixtures thereof.

In a preferred embodiment of the process of the invention, a mixture of water and the amine to be prepared according to the invention or a mixture of water and an organic solvent, preferably a solvent selected from the abovementioned group, is used as solvent at the beginning of the reaction. An advantage of this preferred mode of operation is that foaming of the liquid phase on start-up can be reduced, which in turn allows a smoother start-up.

In a further embodiment of the process of the invention, the liquid phase during start-up comes at least partly from the hydrogenation bath of another reactor, preferably from a reactor which is used for the reaction of the same nitroaromatic with hydrogen to form the corresponding aromatic amine, and/or a product stream before, during or after work-up of such a stream.

The present invention therefore preferably provides the process of the invention in which the liquid phase comes at least partly from the hydrogenation bath of another reactor, preferably from a reactor which is also used for the reaction of the same nitroaromatic with hydrogen to form the corresponding aromatic amine, and/or a product stream before, during or after the work-up of such a stream.

In general, the process of the invention can be carried out at any concentration of at least one nitroaromatic and/or hydrogen which appears suitable, in particular suitable from a safety point of view, to a person skilled in the art.

In a preferred embodiment of the process of the invention, the concentration of nitro groups, i.e. the sum of the product of all nitroaromatics comprised multiplied in each case by the number of their nitro groups per molecule, for example in the case of the hydrogenation of dinitrotoluene (DNT) c(nitroaromatics)=c(DNT)·2+c(ANT)·1 (ANT=aminonitrotoluene), or in the case of the hydrogenation of ortho-nitrotoluene (o-NT) c(nitroaromatics)= c(o-NT)·1, in the liquid phase of the product output from the reactor in the region between the reactor and the preferably downstream product separation unit is from 0 to 2000 ppm by weight, preferably from 0.5 to 1000 ppm by weight, particularly preferably from 1 to 200 ppm by weight and very particularly preferably from 1 to 50 ppm by weight, in each case based on the total weight of the liquid phase of the product output from the reactor. This serves at the same time as a final monitoring of the mixing and reaction processes in the preceding reactors.

Possible ways of setting this concentration according to the invention are known per se to those skilled in the art.

For the purposes of the invention, "liquid phase of the product output in the region between the reactor and the preferably downstream product separation unit" means a liquid stream or a plurality of liquid streams via which the product is discharged from the reactor. The discharge of the product preferably occurs at a place in which DNT concentration is low, i.e. typically downstream of the actual reaction zone, by means of a catalyst separation unit. In the case of stirred tank reactors, a simple overflow is frequently used as catalyst separation unit. In the case of loop reactors or gas recycle reactors, on the other hand, the product is usually discharged from the external loop flow.

Ensuring an appropriate DNT concentration in precisely this "liquid product output in the region between the reactor and the product separation unit" thus serves at the same time as a final monitoring of the mixing and reaction processes in the preceding reactors. Explicit reference is made at this point to the technically much more complicated possibility of ensuring suitable DNT concentrations at various points directly in the reactor. The concentration ranges to be set would in this case increase considerably with increasing proximity to the point of introduction of DNT.

The product or catalyst separation unit is generally a filter (e.g. a membrane filter/crossflow filter), a static decanter (e.g. a gravity separator, frequently a lamellar clarifier) or a dynamic decanter (e.g. a centrifuge or a nozzle separator). The catalyst is separated from the product and subsequently recirculated (generally as a thickened suspension) to the reactor. The discharge of the product is particularly preferably carried out with the catalyst being held back.

The amine can then be purified by conventional, known processes, for example by distillation or extraction.

The analytical monitoring of the DNT concentration in the liquid product output from the reactor in the region between the reactor and the downstream product separation unit on the basis of repeated measurement of the dinitrotoluene concentration in the liquid product output from the reactor is carried out at time intervals of ≤24 hours. The measurement is preferably continually repeated at time intervals of ≤12 hours, particularly preferably ≤4 hours and very particularly preferably ≤1 hour. The time intervals of the monitoring operation are preferably selected so that rapid reaction to changes in the DNT concentration in the region between reactor and product separation unit is possible. The samples taken for monitoring are usually taken upstream of the product separation unit (for example when a settler is used) or downstream of the product separation unit (for example when a filter is used). The measurement of the DNT concentration can be carried out in-line, on-line or off-line.

In a further preferred embodiment of the process of the invention, the hydrogen concentration in the gas phase of the reactor $c(H_2)$ is measured continuously. In a further preferred embodiment, the amount of the gas discharged is set (or regulated) so that $c(H_2)$, i.e. the hydrogen concentration in the gas phase of the reactor, is from 80 to 99% by volume, preferably from 85 to 98% by volume, particularly preferably from 90 to 95% by volume.

The present invention therefore preferably provides the process of the invention in which the hydrogen concentration in the gas phase of the reacvtor is from 80 to 99% by volume, preferably from 85 to 98% by volume, particularly preferably from 90 to 95% by volume.

Many catalysts have been developed for the hydrogenation of nitroaromatics to aromatic amines, in particular of dinitrotoluene to toluenediamine, with improving the yield and selectivity in the reaction and also the stability of the catalysts even at relatively high reaction temperatures having been predominant objectives in the development of new catalysts.

Catalysts which comprise one or more metals selected from the group consisting of platinum, palladium, rhodium, ruthenium and mixtures thereof together with one or more further metals selected from the group consisting of nickel, cobalt, iron, zinc and mixtures thereof as active composition applied to a support have been found to be particularly useful.

Advantageous catalysts are, in particular, catalysts which comprise platinum and also nickel as active composition or else catalysts which comprise palladium, nickel and iron or catalysts which comprise palladium, nickel and cobalt.

Hydrogenation catalysts comprising platinum and nickel on a support in the form of an alloy having an atomic ratio of nickel to platinum in the alloy in the range from 30:70 to 70:30 are particularly advantageous. These are obtained by using platinum and nickel in corresponding amounts in the production of the hydrogenation catalysts. The atomic ratio can be determined, for example, by EDXS (energy dispersive X-ray spectroscopy).

Alloys of platinum and nickel having other atomic ratios can in principle also be used for the process of the invention but lead, particularly when the hydrogenation is carried out at relatively high temperatures, to low yields of aromatic amine.

The catalyst usually comprises finely crystalline metal particles of the Pt—Ni alloy having a size of from about 1 to 15 nm distributed on, for example, carbon particles. Ni—Pt particle agglomerates or aggregates and also single pure Ni or Pt particles can occur in places on the support. The positions of the electron diffraction lines of the metal particles are between those of Pt and Ni, which additionally demonstrates alloy formation. The metal particles are usually polycrystalline and can be characterized by means of high-resolution TEM (FEG-TEM: field emission gun transmission electron microscopy).

As supports for the catalysts, it is possible to use the materials which are customary and known for this purpose. Preferably, activated carbon, carbon black, graphite or metal oxides, preferably hydrothermally stable metal oxides such as $ZrO_2$, $TiO_2$, are used. In the case of graphite, particular preference is given to HSAG (high surface area graphite) having a surface area of from 50 to 300 $m^2/g$. Particular preference is given to physically or chemically activated activated carbon or carbon blacks, e.g. acetylene black.

Further suitable catalysts comprise nickel, either alone or together with at least one metal of transition groups I, V, VI and/or VIII of the Periodic Table, as active component. The catalysts can be produced industrially by application of nickel and optionally at least one of the abovementioned additional metals to a suitable support or by coprecipitation. In this preferred embodiment of the invention, the catalyst has a nickel content in the range from 0.1 to 99% by weight, preferably from 1 to 90% by weight, particularly preferably from 25 to 85% by weight and very particularly preferably from 60 to 80% by weight, based on the total weight of the catalyst. As metals of transition groups I, II, V, VI and/or VIII of the Periodic Table, preference is given to using palladium, platinum, rhodium, iron, cobalt, zinc, chromium, vanadium, copper, silver or a mixture of two or more thereof. As support materials, preference is given to using activated carbon, carbon black, graphite or oxidic support components such as silicon dioxide, silicon carbide, kieselguhr, aluminum oxide, magnesium oxide, titanium dioxide, zirconium dioxide and/or hafnium dioxide or a mixture of two or more thereof, particularly preferably zirconium dioxide, $ZrO_2$, $HfO_2$ and/or $SiO_2$, $ZrO_2$ and/or $SiO_2$, $ZrO_2$, $HfO_2$. Suitable catalysts of this embodiment are described, for example, in the documents EP 1 161 297 A1 and EP 1 165 231 A1.

Nitroaromatics are used as starting material for the process of the invention. In a preferred embodiment of the process of the invention, mononitroaromatics or dinitroaromatics are used, and dinitroaromatics according to the invention are particularly preferably hydrogenated to the corresponding aromatic diamines.

Preferred mononitroaromatics are, for example, selected from the group consisting of nitrobenzene, nitrotoluene, for example 2-nitrotoluene, 3-nitrotoluene and/or 4-nitrotoluene, and mixtures thereof. According to the invention, nitrobenzene can be hydrogenated to aniline. Furthermore, nitrotoluene can be hydrogenated to the corresponding toluidenes.

Preferred nitroaromatics are, for example, selected from the group consisting of dinitrobenzene, for example 1,2-dinitrobenzene, 1,3-dinitrobenzene and/or 1,4-dinitrobenzene, dinitrotoluene and mixtures thereof. According to the invention, dinitrobenzene can be hydrogenated to diaminobenzene. Furthermore, dinitrotoluene can be hydrogenated to the corresponding toluenediamine isomers.

According to the invention, preference is given to using dinitrotoluene (DNT). Dinitrotoluene is known per se to those skilled in the art and can be present in various isomers which are depicted below:

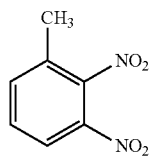

(Ia)

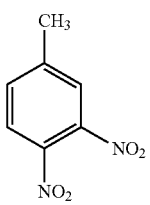

(IIa)

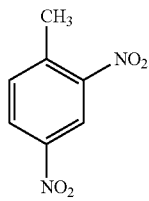

(IIIa)

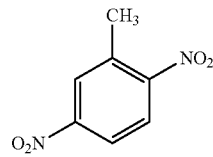

(IVa)

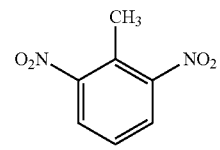

(Va)

According to the invention, it is possible to use a single isomer selected from among 2,3-dinitrotoluene (Ia), 3,4-dinitrotoluene (IIa), 2,4-dinitrotoluene (IIIa), 2,5-dinitrotoluene (IVa) and 2,6-dinitrotoluene (Va). However, it is also possible according to the invention, and preferred, to use a mixture comprising at least two of the isomers mentioned, for example a mixture comprising 2,4-dinitrotoluene (IIIa) and 2,6-dinitrotoluene (Va). In a preferred embodiment of the process of the invention, a mixture of dinitrotoluene isomers as is obtained in the double nitration of toluene is used.

In a preferred embodiment, the corresponding toluenediamines are obtained as product of the process of the invention after hydrogenation. The possible isomers are depicted below.

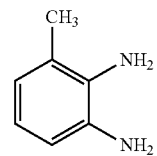

(Ib)

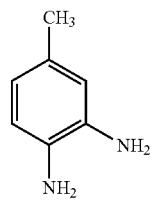

(IIb)

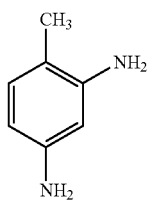

(IIIb)

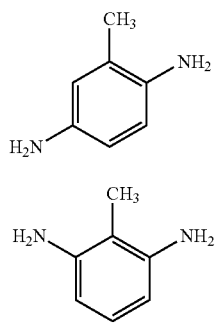

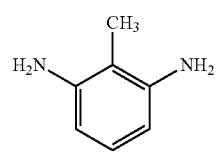

Depending on which isomer or which isomers of dinitrotoluene is/are used as starting material, a corresponding isomer or a mixture of at least two isomers of toluenediamine is obtained as product of the process of the invention, i.e. preferably no isomerization and/or hydrogenation of the aromatic system takes place during the reaction according to the invention.

Possible products are therefore selected from among toluene-2,3-diamine (Ib), toluene-3,4-diamine (IIb), toluene-2,4-diamine (IIIb), toluene-2,5-diamine (IVb) and toluene-2,6-diamine (Vb). However, it is also possible according to the invention, and preferred, for a mixture comprising at least two of the isomers mentioned, for example a mixture comprising toluene-2,4-diamine (IIIb) and toluene-2,6-diamine (Vb), to be obtained. Furthermore, it is possible for compounds in which only one nitro group has been hydrogenated to the corresponding amino group and one nitro group still remains in the molecule to be present in the product mixture obtained.

The process is preferably carried out at space-time yields of from 100 to 1000 kg·m$^{-3}$ h$^{-1}$, preferably from 200 to 600 kg m$^{-3}$·h$^{-1}$, of aromatic amine. Here, the reaction volume in m$^3$, corresponding to the total volume of the reactor minus the volume of internals present therein and the gas volume, is used in the calculation.

The process of the invention is preferably carried out in a vertical reactor. The length of the reactor is preferably greater than the width. Suitable dimensions can easily be determined by a person skilled in the art.

The process of the invention is preferably carried out in a reactor in which internal and external loop motion of the reaction mixture takes place. Suitable reactors are described, for example, in the European patent application EP 11 158 462.9 or in the document WO 00/35852.

For this purpose, a driving jet nozzle is installed at the upper end of a preferably vertical reactor so as to drive the internal loop motion, preferably by the reaction mixture taken off at the bottom of the reactor, which is pumped through an external loop, being injected in a downward direction into the upper region of the reactor via the driving jet nozzle.

The reaction mixture injected via the driving jet nozzle preferably flows through a central plug-in tube arranged in the longitudinal direction of the reactor and flows through this from the top downward. The central plug-in tube can be configured as a simple tube. Below the plug-in tube, the reaction mixture reverses its direction in an internal loop motion outside the plug-in tube and flows upward again.

To effect flow reversal, an impingement plate is preferably arranged below the plug-in tube.

The preferably concentric plug-in tube in combination with the impingement plate which is preferably present stabilizes the loop flow within the reactor, i.e. the internal loop flow.

Gas from the gas space is entrained in the form of gas bubbles in the liquid and carried to the impingement plate by the driving jet. These gas bubbles rise again in the annular space, i.e. between plug-in tube and reactor wall, of the reactor. This internal gas recycle operation provides a large gas/liquid phase interface.

To remove heat, a heat exchanger through which cooling water flows and takes up part of the heat of reaction is preferably arranged in the interior of the reactor. The heat exchanger arranged in the interior of the reactor is preferably a field tube heat exchanger. In an embodiment, the heat exchanger arranged in the interior of the reactor is a coil heat exchanger. In a further embodiment, the heat exchanger arranged in the interior of the reactor is a shell-and-tube heat exchanger. In a further embodiment, the heat exchanger arranged in the interior of the reactor is a plate heat exchanger.

In a preferred embodiment of the process of the invention, a further heat exchanger is used in the external loop in addition to the heat exchanger arranged in the interior of the reactor. This second heat exchanger which is preferably present preferably serves to remove the remainder of the heat of reaction which cannot be removed via the internal heat exchanger. A shell-and-tube heat exchanger is preferably used.

Steam can be generated from the heat of reaction liberated in two ways both in the internal heat exchanger and in the external heat exchanger. Firstly by vaporation of part of the cooling water in the cooling tubes (direct steam generation) or by heating the cooling water at a pressure which is above the pressure of the steam to be generated and subsequent depressurization to the pressure level of the steam to be generated (flash evaporation). In this depressurization, part of the cooling water vaporizes and the steam/water mixture is cooled to the boiling temperature corresponding to the pressure of the steam.

Both types of vaporization can be employed both in the internal heat exchanger and in the external heat exchanger. A combination of the two types of vaporization, i.e. direct vaporization in the internal heat exchanger and flash evaporation in the external heat exchanger, or vice versa, is likewise possible.

However, depending on, for example, the reaction temperature, steam generation can also be dispensed with and the heat can be taken up by recooling water.

Nitroaromatics are preferably introduced at the upper end of the reactor, preferably into the gas phase above the surface of the liquid in the reactor.

In a preferred embodiment of the process of the invention, introduction of the nitroaromatic is effected through a feedline and/or a metering device.

In the process, it is preferred that, at the correct fill height of the reactor, direct physical contact between the feed device for the nitroaromatic and the liquid phase, preferably comprising the desired aromatic amine, water and catalyst, in the reactor and/or in the pump circuit can occur neither in the operating state nor on shutdown.

For the present purposes, a correct fill height is a fill height having a liquid surface between the upper edge of a plug-in tube which is preferably present and the outlet opening of the driving jet nozzle. The liquid surface is preferably closer to the outlet opening of the driving jet nozzle than to the upper edge of the plug-in tube.

In a preferred embodiment of the process of the invention, the total system is made of steel which does not rust, hereinafter referred to as stainless steel, since steels which rust, known as black steels, tend to form corrosion products which can lead to increasing transmembrane pressures when membranes are used as catalyst separation unit.

In the embodiment according to the invention in which nitroaromatics are hydrogenated over nickel catalysts, the use of black steel can prove to be particularly preferred. In this variant, which is cheaper compared to stainless steel, rust formation (iron(II) oxide, iron(III) oxide and water of crystallization) has a positive effect on the catalysis due to the additional iron-promoting effect. In this case, a gravity separator, for example, is used as separation device.

In a preferred embodiment of the process of the invention, the introduction of the nitroaromatic is effected via a feedline or a metering device without the geometric possibility of dead space formation. Appropriate units and apparatuses are known per se to those skilled in the art. According to the invention, it is essential that, at the correct fill height of the reactor, direct physical contact between the feed device for the nitroaromatic and the liquid phase, preferably comprising the aromatic amine, i.e. the corresponding reaction product, water and catalyst, in the reactor and/or in the pump circuit can occur neither in the operating state nor on shutdown. According to the invention, this is achieved, for example, by the distance between the feed device for the nitroaromatic and the liquid phase being, for example, from 0.01 to 3 m, preferably from 0.05 to 1.0 m.

In a further preferred embodiment of the process of the invention, introduction of the nitroaromatic is effected via one or more independent pipes, the partial or complete blocking of which can be measured. Appropriate pipes are known per se to those skilled in the art. The pipes which are preferably used are made, for example, of metal, for example black steel or stainless steel. The pipes preferably have diameters determined by the amounts of nitroaromatics which are introduced.

In general, the pipes which are preferably used can have any suitable cross section. In a preferred embodiment of the process of the invention, the outlet cross section of the feed device for the nitroaromatic has a constriction at the ends of the one or more independent pipe(s). The exiting nitroaromatics jet can have laminar or turbulent behavior.

It is also advantageous according to the invention for significant local overconcentrations to be avoided when mixing the freshly introduced nitroaromatic into the reaction mixture. Increased (local) concentrations of nitroaromatics lead to increased by-product formation and deactivation of the suspended catalyst. This results in a decrease in yield and thus a greater outlay for work-up of the product and also increased catalyst costs and capacity decreases. In addition, safety problems can occur.

The driving jet of the external circuit preferably brings about circulating flow in the interior of the reactor. The downflow region of this circulating flow is defined by the cross-sectional area of the plug-in tube which is preferably present parallel to the reactor axis. The upflow region is defined by the cross-sectional area of the annular gap between the plug-in tube which is preferably present and the reactor wall.

The driving jet of the external circuit preferably spreads out as a turbulent free jet in the reaction medium. At the circumference of a turbulent free jet, acceleration and mixing-in of the surrounding fluid takes place as a result of momentum input.

When nitroaromatics are applied to the liquid surface in the interior of the reactor, the effectiveness of mixing-in is accordingly improved with increasing proximity to the impingement region of the driving jet on the liquid surface. The effectiveness of mixing-in determines the spatial extension of the mixing-in zone and also the height of the nitroaromatic overconcentration occurring in a steady state therein compared to the total reactor volume.

In the preferred embodiment according to the invention in which the reactor used according to the invention has a central plug-in tube arranged in the longitudinal direction of the reactor, a laminar or turbulent nitroaromatic jet from one or more of the feed devices for the nitroaromatic impinges, in the process of the invention, onto the surface of the liquid phase in the region of the cross-sectional area of the plug-in tube projected onto the liquid surface, preferably close to the driving jet of the nozzle of the external circuit, particularly preferably directly at the circumference of the driving jet of the nozzle of the external circuit.

In a further preferred embodiment of the process of the invention, the outlet openings of the one or more feed devices for the nitroaromatic are inclined by up to 90° in the direction of the axis of symmetry of the reactor in order to generate a radial impulse. In this embodiment, the outlet openings are inclined by, for example, from 10 to 80°, preferably from 10 to 45°, in the direction of the axis of symmetry of the reactor.

The process of the invention preferably has the feature that partial or complete blocking of the feed device for the nitroaromatic can be measured after undesirable contact between the feed device for the nitroaromatic and the liquid phase of the reactor.

Measurement methods and apparatuses for measuring such blocking are known per se to those skilled in the art, for example pressure gauges or flow meters. For example, blocking can be detected by a mass flow decreasing at a constant pressure difference. Furthermore, blocking can be detected, for example, by a rise in the pressure at the corresponding place at a constant mass flow.

The hydrogen required for the hydrogenation is introduced at the lower end of the reactor, preferably by a ring distributor.

A further preferred feature of the process of the invention is that the concentration of hydrogen in the reaction mixture which flows from the bottom of the reactor into the external loop does not go below 0.1% by volume, preferably 3% by volume. This minimum concentration according to the invention in the reaction mixture ensures, for example, that a desirable high conversion of the nitroaromatic, preferably the dinitrotoluene, and thus a low nitroaromatic concentration, preferably dinitrotoluene concentration, are also achieved in the region of the external circuit.

In a further preferred embodiment of the process of the invention, additional hydrogen is introduced into the reaction mixture flowing in the external loop, preferably very close to the reactor, in order to ensure the minimum concentration of hydrogen in the external loop, i.e. in the pump circulating stream.

In a further preferred embodiment of the process of the invention, hydrogen is introduced into the reactor at any place and the reactor diameter or the outflow rate of the reaction mixture from the bottom of the reactor is designed so that the minimum concentration of hydrogen in the external loop is ensured. The outflow rate of the reaction mixture can be influenced by measures known to those skilled in the art, for example a suitable configuration of the reactor diameter.

To be able to drive the external circuit, a pump which can transport not only liquid but also gas and suspended solid is preferably installed. Here, up to 20% by volume of gas and 20% by weight of suspended solid should be pumpable.

The reaction temperature of the process of the invention is generally from 50 to 250° C., preferably from 80 to 200° C., particularly preferably from 110 to 190° C., for example from 110 to 130° C. or from 170 to 190° C.

The reaction pressure in the process of the invention is generally from 5 to 50 bar absolute, preferably from 10 to 50 bar absolute, particularly preferably from 10 to 40 bar absolute, very particularly preferably from 20 to 35 bar absolute.

EXAMPLES

Example 1

For the catalytic hydrogenation of DNT to TDA, a cylindrical loop reactor having an external circuit driven by two centrifugal pumps with double-acting sliding ring seal and barrier pressure device connected in series and ending in a driving jet nozzle arranged centrally at the top of the reactor, a concentric plug-in tube and an impingement plate in the lower part of the reactor to divert the loop flow (internal circuit) was used (for the functional principle, cf. WO2000/35852 A1). The reaction volume of the reactor was about 14 m$^3$. The reactor was provided with a tube bundle comprising field tubes connected in parallel to remove the heat of reaction. It had a jacket for heating with 2.5 bar gauge steam. The amount of cooling water fed into the field tubes and/or (during interruption of the reaction of DNT and during start-up and shutdown processes) the amount of steam passed through the jacket was/were set so that the reactor temperature was maintained at from 115 to 120° C. in the region of the field tubes.

To maintain the loop flow, a volume stream of 630 m$^3$/h was circulated in the external product circuit, as a result of which a pressure drop of about 2.7 bar was established over the driving jet nozzle. The reactor comprised about 12 m$^3$ of a liquid hydrogenation bath. This consisted essentially of a mixture of TDA (including by-products) and water in a mass ratio of 0.57:0.43 in which about 7% by weight of a metallic Ni catalyst supported on $SiO_2$ and $ZrO_2$ (produced as described in example 2 of EP 1 161 297 and comminuted by means of a stirred ball mill; here, 10% by volume of the catalyst consisted of particles having a diameter of <about 4 μm (d10), 50% by volume are <about 13 μm ($d_{50}$) and 90% by volume are <about 19 μm ($d_{50}$), measured by means of laser light scattering (Malvern Mastersizer S) after stirring up in water) was suspended and in which hydrogen was also dissolved. The liquid surface was just below the opening of the driving jet nozzle. Above this, there was about 2 m of a gas atmosphere whose hydrogen content was set to about 95% by volume (apart from inert gases such as $N_2$) by continuous discharge of a small offgas stream.

An amount of hydrogenation product was continuously taken off from the external product circuit on the pressure side of the second centrifugal pump and fed into a lamellar clarifier having a liquid volume of about 50 m$^3$ and a gas volume of about 10 m$^3$. The catalyst was able to concentrate in the lower region of this clarifier. About 18 m$^3$/h of an appropriately thickened suspension were then recirculated to the suction side of the first centrifugal pump.

During interruptions to the introduction of DNT, the amount of hydrogenation product fed to the lamellar clarifier was likewise about 18 m$^3$/h; otherwise, it was increased as a function of the introduction of DNT in order to keep the liquid level in the reactor constant. At the same time, up to 7.6 t/h of hydrogenation product were taken off from the lamellar clarifier via an overflow. This comprised about 56% by weight of TDA (with an isomer distribution corresponding to that of the DNT used), about 1% by weight of low and high boilers (in a ratio of about 20:80) and about 43% by weight of water and about 0.01% by weight of catalyst (mainly fines). The hydrogenation product went, like the hydrogenation products of other reactors, via a pressure reduction to a common intermediate vessel and was continuously conveyed from this to the work-up by distillation. The parts in contact with product were partly made of black steel (generally St 37) and partly of stainless steel (1.4571).

During the introduction of DNT, 0.6 t/h of a suspension of the abovementioned catalyst in water (partly separated off from the hydrogenation product in the work-up section) were metered continuously by means of a membrane pump into the reactor. The amount of fresh catalyst comprised in this suspension was on average about 1 kg/h. Molten DNT heated to about 80° C., consisting of a mixture of the 2,4- and 2,6-DNT isomers in a ratio of about 80:20 and also about 5% of the other DNT isomers and traces of mononitrotoluene was injected by means of a diaphragm piston metering pump into the gas space of the reactor. At the same time, hydrogen (diluted with about 0.1% of $N_2$ and also traces of methane, CO and inerts) was, controlled by a pressure regulator, introduced via a nozzle ring above the impingement plate in such an amount that the pressure was kept virtually constant in the range from 24.9 to 25.1 bar gauge.

Commencing at 4 t/h at time 2 hours, the introduction of DNT was increased stepwise as shown in FIG. 1. The amount of hydrogen introduced rose in parallel thereto. A brief decrease in the amount of hydrogen after 6 hours, indicating incomplete conversion, could be compensated by reducing the amount of DNT introduced. The decrease in the amount of hydrogen was accompanied by a drop in the temperature at the reactor outlet and an increase in the temperature difference over the external circuit from 0.0 K up to 1.7 K; correspondingly, incomplete conversion in the reactor and a corresponding after-reaction in the external circuit can be concluded. In normal operation, the temperature in the external circuit was virtually constant at about 126° C. In the reactor, the temperature at the lower end of the plug-in tube was about 125° C.; cooling to about 119° C. then occurred by means of the field tubes. After 9 hours, the hydrogen uptake began to fluctuate significantly; after 10 hours it, and thus also the conversion in the reactor, dropped normally. When the hydrogen uptake (amount of hydrogen introduced−amount of offgas) went below 50% of the amount required for the stoichiometric reaction of DNT to form TDA, the introduction of DNT was interrupted according to the invention.

To determine the content of DNT and ANT (aminonitrotoluene=partially hydrogenated intermediate) in the hydrogenation bath, samples of suspension were taken off from the line from the external product circuit of the loop reactor to the lamellar clarifier after about 3, 7 and 10 hours. These were freed of suspended solid by filtration and the concentration of the nitro compounds comprised was determined by means of polarography. In the first two samples, the DNT concentration was 13 and 15 ppm, respectively, and the ANT concentration was in each case 3 ppm. However, the sample taken shortly before interruption of the introduction of DNT comprised 84 ppm of DNT and 3640 ppm of ANT. Owing to the duration of the analysis, this result was, however, available only after about 1 hour after the interruption of the introduction of DNT.

Owing to the timely interruption according to the invention of the introduction of DNT, there was no appreciable damage to the catalyst. After introduction of an additional about 20 kg of fresh catalyst, the reactor could be started up again as per example 2 and operated stably for a prolonged period.

Example 2

The loop reactor as per example 1 was used for the catalytic hydrogenation of DNT to TDA. The amount of cooling water fed into the field tubes and/or (during interruption of the reaction of DNT and during start-up and shutdown processes) the amount of steam passed through the jacket was/were again set so that the reactor temperature was maintained at from 115 to 120° C. in the region of the field tubes.

To maintain the loop flow, a volume stream of 630 m$^3$/h was circulated in the external product circuit, as a result of which a pressure drop of about 2.7 bar was established over the driving jet nozzle. The reactor comprised about 12 m$^3$ of the liquid hydrogenation bath from example 1 and the additional 20 kg of fresh catalyst introduced. The liquid surface was just below the opening of the driving jet nozzle. Above this, there was about 2 m$^3$ of a gas atmosphere whose hydrogen content was set to about 95% by volume (apart from inert gases such as N$_2$) by continuous discharge of a small offgas stream.

An amount of hydrogenation product was continuously taken off from the external product circuit on the pressure side of the 2$^{nd}$ centrifugal pump and fed into the lamellar clarifier from example 1. The catalyst was able to concentrate in the lower region of this clarifier. About 18 m$^3$/h of an appropriately thickened suspension were then recirculated to the suction side of the first centrifugal pump. During interruptions to the introduction of DNT, the amount of hydrogenation product fed to the lamellar clarifier was likewise about 18 m$^3$/h; otherwise, it was increased as a function of the introduction of DNT in order to keep the liquid level in the reactor constant. At the same time, up to 7.3 t/h of hydrogenation product were taken off from the lamellar clarifier via an overflow. This comprised about 56% by weight of TDA (with an isomer distribution corresponding to that of the DNT used), about 1% by weight of low and high boilers (in a ratio of about 20:80) and about 43% by weight of water and about 0.01% by weight of catalyst (mainly fines). The hydrogenation product went, like the hydrogenation products of other reactors, via a pressure reduction to a common intermediate vessel and was continuously conveyed from this to the work-up by distillation.

During the introduction of DNT, 0.6 t/h of a suspension of the abovementioned catalyst in water (partly separated off from the hydrogenation product in the work-up section) were metered continuously by means of a membrane pump into the reactor. The amount of fresh catalyst in this suspension was on average about 2 kg/h. Molten DNT heated to about 80° C., consisting of a mixture of the 2,4- and 2,6-DNT isomers in a ratio of about 80:20 and also about 5% of the other DNT isomers and traces of mononitrotoluene was injected by means of a diaphragm piston metering pump into the gas space of the reactor. At the same time, hydrogen (diluted with about 0.1% of N$_2$ and also traces of methane, CO and inerts) was, controlled by a pressure regulator, introduced via a nozzle ring above the impingement plate in such an amount that the pressure was kept virtually constant in the range from 24.9 to 25.1 bar gauge. From an amount of DNT of 5 t/h, an additional 320 standard m$^3$/h of hydrogen were metered into the external product circuit at the reactor output.

Figure 2:
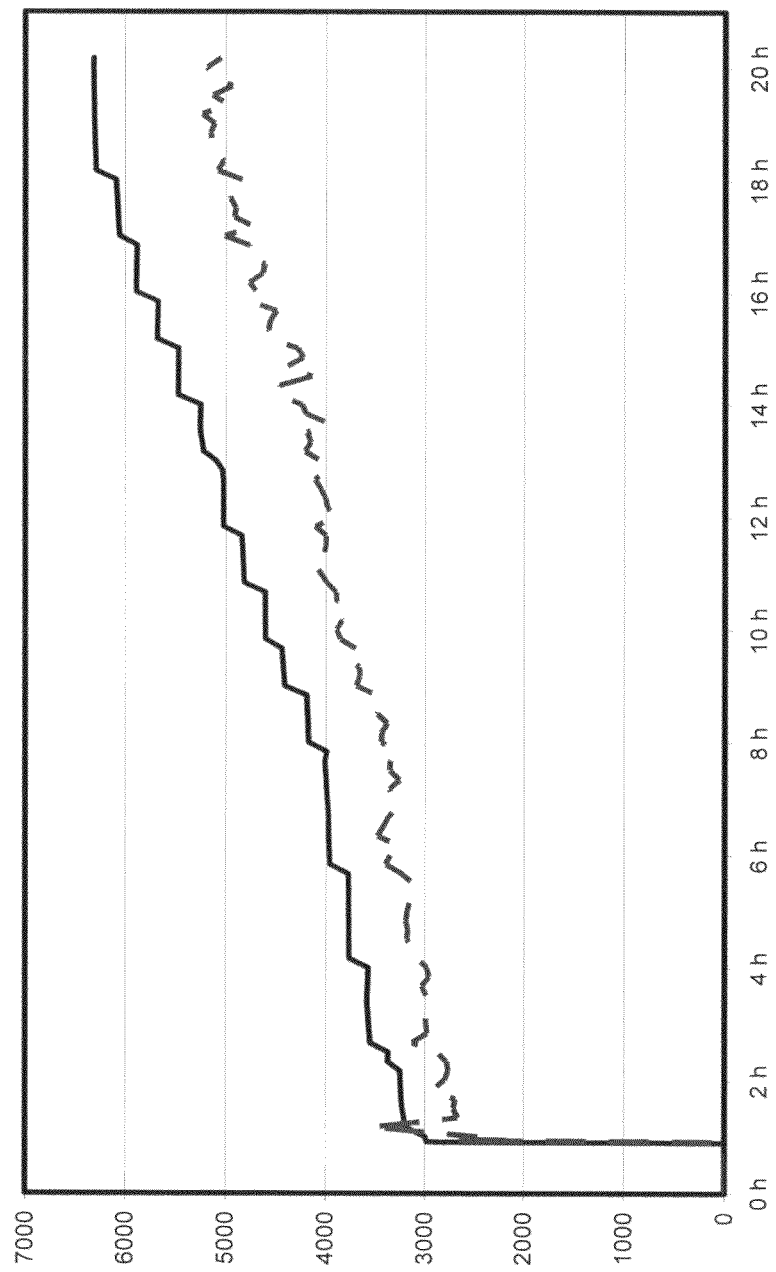
FIG. 2 shows the amount of DNT used (solid line, in kg/h) and amount of hydrogen introduced (broken line, in standard m$^3$/h) versus time in hours for example 2.

Commencing at 3 t/h at time 1 hours, the introduction of DNT was increased more slowly and in smaller steps than in example 1 as shown in FIG. 2. The amount of hydrogen introduced increased in parallel with this. The temperature in the external circuit was virtually constant at about 126° C. In the reactor, at the lower end of the plug-in tube it was about 125° C.; cooling to about 119° C. then occurred by means of the field tubes.

To determine the content of DNT and ANT in the hydrogenation bath, samples of suspension were taken off from the line from the external product circuit of the loop reactor to the lamellar clarifier after about 1, 2, 3, 4, 5, 8, 12, 16 and 20 hours. These were freed of suspended solid by filtration and the concentration of the nitro compounds comprised was determined by means of polarography. Here, the DNT concentration was in the range from 9 to 28 ppm and the ANT concentration was in the range from 3 to 12 ppm. Nothing conspicuous was observed and operation could be continued without problems for a number of days.

Example 3

A stirred tank reactor (diameter: 2.8 m, height: 4.7 m, volume: 23 m$^3$, material: St37) having internal cooling coils affixed in the region of the reactor wall was used for the catalytic hydrogenation of o-nitrotoluene to o-toluidine. Its stirrer, which was driven by an electric motor via V-belts, comprised a turbine stirrer (d=790 mm) having a hollow shaft which distributed the hydrogen in the hydrogenation bath. A small bladed wheel having three blades (d=250 mm) below the turbine drew in the thickened suspension flowing back from the decanting vessel used here and pushed it upwards into the flow generated by the turbine. The speed of rotation of the stirrer was a constant 450 min$^{-1}$. The sealing of the shaft to the reactor was effected by means of a double-acting sliding ring seal with barrier pressure device.

The amount of cooling water fed into the cooling coils was set so that the temperature in the reactor was maintained at about 93° C. The reactor comprised about 18 m$^3$ of a liquid hydrogenation bath. This consisted essentially of a mixture of o-toluidene, methanol and water in a mass ratio of 0.50:0.27:0.23 in which about 1.4% by weight of the metallic Ni catalyst supported on SiO$_2$ and ZrO$_2$ mentioned in example 1 was suspended and hydrogen was also dissolved. Above the liquid surface, there were about 5 m$^3$ of a gas atmosphere whose hydrogen content was set to from 92 to 95% by volume (apart from inert gases such as N$_2$) by continuous discharge of a small offgas stream.

To keep the level of liquid in the reactor constant, a corresponding amount of hydrogenation product was taken off continuously via an overflow and introduced into a decanting vessel having a liquid volume of about 16 m$^3$ and a gas volume of about 4 m$^3$. The catalyst was able to concentrate in the lower region of this. About 16 m$^3$/h of a correspondingly thickened suspension were then sucked back into the stirred tank by means of the bladed wheel of the stirrer. During the hydrogenation, up to 1.7 t/h of hydrogenation product were taken off from the decanting vessel via an overflow. This comprised about 50% by weight of o-toluidine, considerably less than 1% by weight of low and high boilers, about 27% by weight of methanol and about 23% by weight of water and traces of the catalyst (mainly fines). The hydrogenation product went via a pressure reduction into an intermediate vessel and from this was continuously fed to the work-up by distillation.

During the introduction of o-nitrotoluene, 0.6 m$^3$/h of a suspension of the above-mentioned catalyst in methanol (partly separated off from the hydrogenation product in the work-up section and still comprising residual water) was metered continuously into the reactor by means of a diaphragm pump. The amount of fresh catalyst in this suspension was on average about 0.2 kg/h. Liquid o-nitrotoluene was introduced into the gas space of the reactor by means of a diaphragm piston metering pump. Controlled by a pressure regulator, hydrogen (diluted with about 0.1% of N$_2$ and traces of methane, CO and inerts) was at the same time introduced so that the pressure was kept virtually constant in the range from 22.5 to 23.5 bar gauge.

Figure 3:
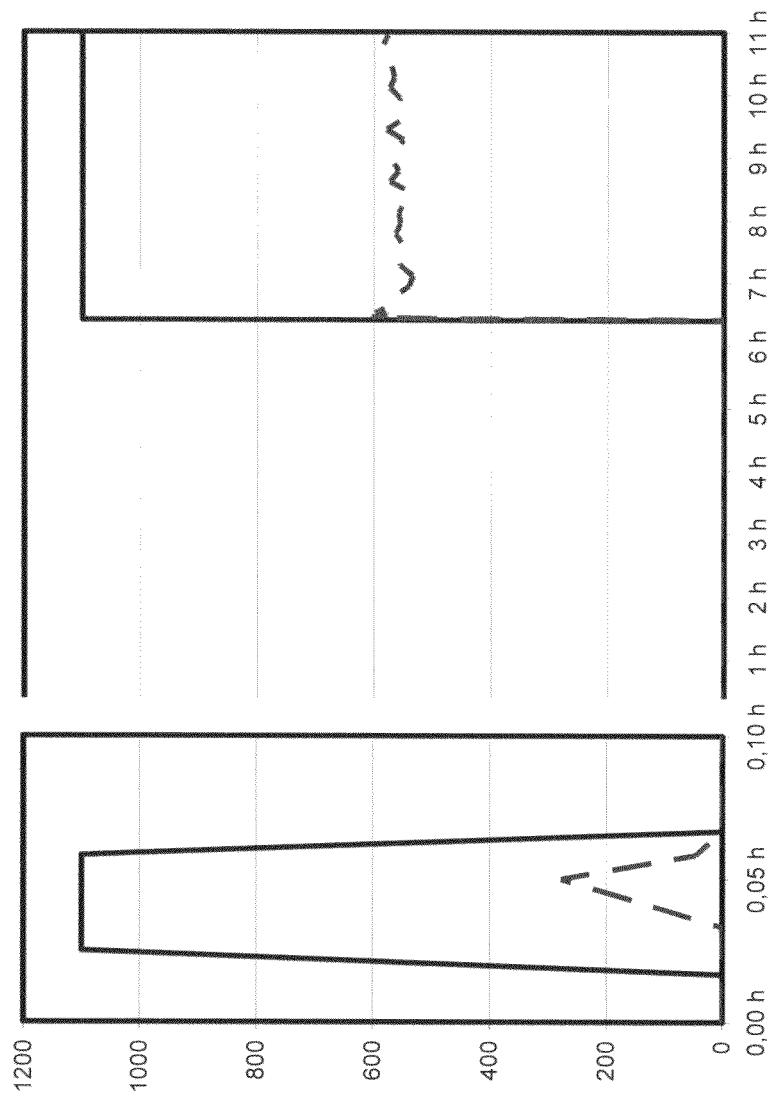
FIG. 3 shows the amount of o-NT used (solid line, in kg/h) and amount of hydrogen introduced (broken line, in standard m$^3$/h) versus time in hours for example 3.

The course of the amount of o-nitrotoluene fed in and also the amount of hydrogen introduced is shown in FIG. 3: In a first start-up experiment, 1100 kg/h of o-nitrotoluene were metered in at the beginning for about 3 minutes. Since the hydrogen uptake (amount of hydrogen introduced−amount of offgas) did not reach 50% of the amount required for the stoichiometric reaction of o-nitrotoluene to form o-nitrotoluidene within this time because of contamination in the hydrogen line, the introduction of o-nitrotoluene was then interrupted according to the invention. After elimination of the contamination, a further start-up experiment using 1100 kg/h of o-nitrotoluene was carried out about 6 hours later; in this, the hydrogen uptake swiftly achieved the amount of about 570 standard $m^3/h$ required for the stoichiometric reaction of o-nitrotoluene to form o-toluidene (cf. FIG. 3). The reaction proceeded under largely isothermal conditions.

To determine the o-nitrotoluene content in the hydrogenation bath, samples of suspension were taken off from the line from the stirred tank reactor to the decanting vessel, firstly at intervals of 30 minutes and later at intervals of 4 hours. These were freed of suspended solid by filtration and the o-nitrotoluene content was determined by means of polarography. This was not more than 3 ppm at any point in time. Nothing conspicuous was observed and operation could be continued without problems for a number of weeks.

Example 4

A jacket-heated stirred tank reactor (volume: 2.2 l, material: 1.4571) having an internal cooling coil and a disk stirrer was used for the catalytic hydrogenation of DNT to TDA. The reactor comprised 1.3 l of water in which 0.2 g of the Ni catalyst as per example 1 (as a difference, 50% by volume <about 6 μm ($d_{50}$)) were suspended and hydrogen was also dissolved and also a hydrogen atmosphere above the liquid surface. The reactor was regulated to a temperature of 130° C. and operated at a stirrer speed of 1500 $min^{-1}$ in the semibatch mode without discharge. Various amounts of molten DNT maintained at a temperature of about 80° C. were metered into the reactor by means of a HPLC pump (piston metering pump). At the same time, hydrogen was introduced under control by a pressure regulator so that the pressure was kept virtually constant at about 25 bar gauge. The amounts of hydrogen introduced in this way by means of the hydrogen metering unit and DNT metered in by means of the HPLC pump were continuously monitored and an amount of accumulated DNT was calculated from the difference from the amount of hydrogen required for the stoichiometric reaction of DNT to form TDA. The termination criterion for the introduction of DNT was, for safety reasons, a free DNT content of 1% by weight (decrease in the onset temperature of the reaction mixture with increasing DNT concentration). A restart of the introduction of DNT was then possible only after the accumulated DNT had reacted. For this purpose, the introduction of hydrogen remained in operation. Unreacted DNT was thus able to react with hydrogen to form the amine. This gives the time offset (delay) until restarting of the introduction of DNT which is shown in FIG. 4 and FIG. 5.

Figure 4:
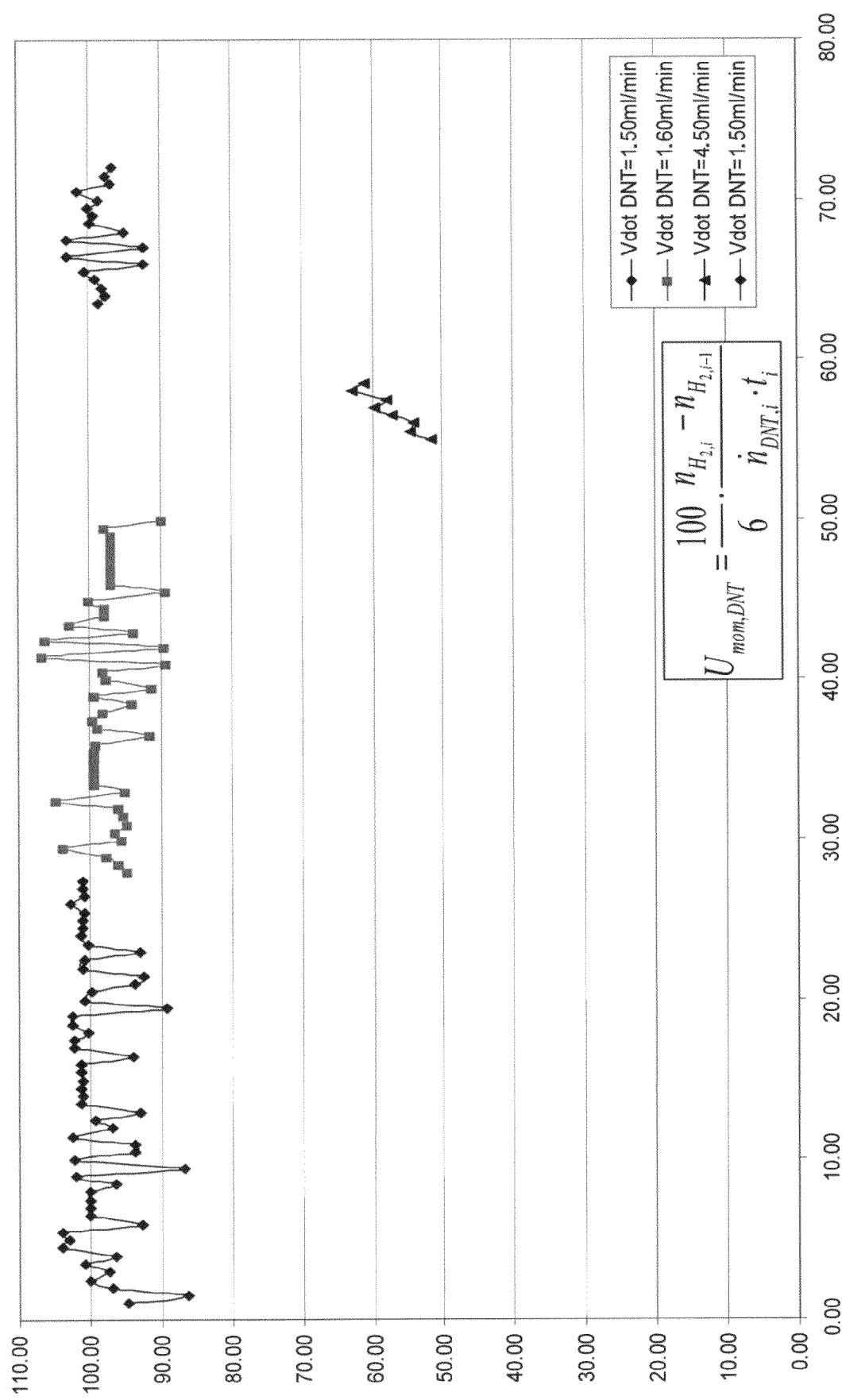
FIG. 4 shows the conversion of DNT in percent at different amounts of DNT in a laboratory reactor versus time in minutes for example 4.
Figure 5:
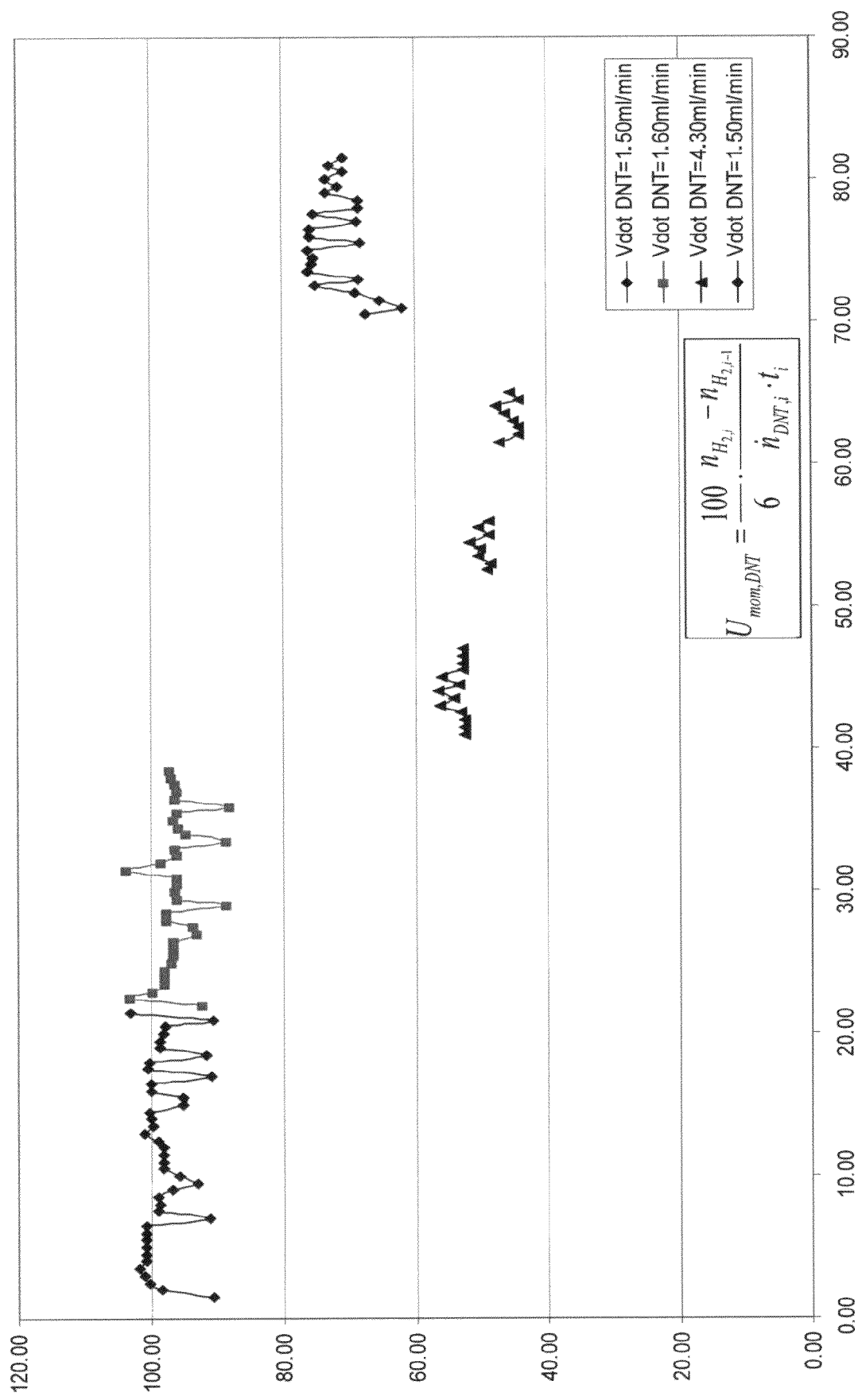
FIG. 5 shows the conversion of DNT in percent at different amounts of DNT in a laboratory reactor versus time in minutes corresponding to comparative example 1.

After activation of the catalyst for 30 minutes at 130° C. and 25 bar gauge, the introduction of DNT was started, as shown in FIG. 4, firstly under standard conditions (1.5 ml/min). Here, a conversion of 100% (hydrogen uptake corresponding to the amount required for the stoichiometric reaction of DNT to form TDA) was achieved. The amount of DNT metered into the reactor by means of the HPLC pump was then firstly increased stepwise from 1.5 to 4.5 ml/min. At this maximum load, a conversion of only 50-60% was achieved. After 5 minutes at this low conversion, the introduction of DNT was stopped according to the invention. The subsequent repetition of the introduction of DNT under standard conditions (1.5 ml/min) again led to a conversion of 100% and thus shows that damage to the catalyst was able to be prevented by the rapid termination of the introduction of DNT according to the invention.

Comparative Example 1

The laboratory experiment of example 4 was repeated, but the introduction of DNT was carried out at maximum load (here 4.3 ml/min) in this case for a total of 15 minutes, of which 10 minutes was at a conversion of ≤50% (hydrogen uptake <50% of the amount required for the stoichiometric reaction of DNT to form TDA)—i.e. considerably longer than is permissible according to the invention. The subsequent repetition of the introduction of DNT under standard conditions (1.5 ml/min) led in this case to a conversion of only about 75% (see FIG. 5), i.e. irreversible damage to the catalyst occurred during the 10 minutes of introduction of DNT at a conversion of <50%, presumably due to oxidative poisoning by nitroaromatic compounds (DNT or nitroaromatic intermediates such as ANT).

The invention claimed is:

1. A continuous process for preparing at least one aromatic amine, the process comprising hydrogenating of at least one nitroaromatic with hydrogen in a reactor, in the presence of a liquid phase comprising at least one aromatic amine and a gas phase comprising at least the hydrogen, in the presence of a catalyst suspended in the liquid phase at a temperature of from 50 to 250° C. and at a pressure of from 5 to 50 bar,
wherein:
   the pressure in the reactor is maintained essentially constant by continuously adapting an amount of hydrogen fed to the reactor;
   a total amount of the hydrogen fed to the reactor is monitored; and
   introduction of the at least one nitroaromatic to the reactor is interrupted if hydrogen uptake in the reactor is not at least 50 mol %, of an amount of hydrogen required for stoichiometric reaction of the at least one nitroaromatic to form the at least one aromatic amine.

2. The process according to claim 1, wherein the hydrogen uptake in the reactor corresponding to the stoichiometric reaction of the at least one nitroaromatic is reached not more than 5 minutes after commencement of the introduction of the nitroaromatic.

3. The process according to claim 1, wherein:
   toluenediamine is prepared from dinitrotoluene; or
   toluidene is prepared from nitrotoluene;
   or aniline is prepared from nitrobenzene.

4. The process according to claim 1, wherein the at least one nitroaromatic is introduced to the reactor by stepwise or continuous introduction over a period from 0.5 to 120 hours after the start of the process.

5. The process according to claim 1, wherein the liquid phase further comprises at least one solvent selected from the group consisting of water, an organic solvent, an aromatic amine formed during process, and a mixture thereof.

6. The process according to claim 1, wherein the liquid phase is obtained at least partly from a hydrogenation bath of a separate reactor, and/or from a product stream withdrawn before, during or after work-up of a product formed in the separate reactor.

7. The process according to claim 1, wherein a hydrogen concentration in the gas phase is from 80 to 99% by volume.

8. The process according to claim 1, wherein the introduction of the at least one nitroaromatic is commenced with from 10 to 90 mol % of a total amount of the at least one nitroaromatic introduced in the process.

9. The process according to claim 8, wherein an amount of the at least one nitroaromatic introduced is increased stepwise or continuously during the hydrogenation.

10. The process according to claim 1, wherein a concentration of nitro compounds is from 1 to 200 ppm.

11. The process according to claim 1, wherein the introduction of the at least one nitroaromatic to the reactor is interrupted if the hydrogen uptake in the reactor is not at least 90 mol % of the amount of hydrogen required for stoichiometric reaction of the at least one nitroaromatic to form the at least one aromatic amine.

12. The process according to claim 1, wherein toluenediamine is prepared from dinitrotoluene.

13. The process according to claim 1, wherein toluidene is prepared from nitrotoluene.

14. The process according to claim 1, wherein aniline is prepared from nitrobenzene.

15. The process according to claim 1, wherein the liquid phase is obtained at least partly from a hydrogenation bath of a different reactor, in which the at least one nitroaromatic is hydrogenated to form the at least one aromatic amine, and/or from a product stream withdrawn before, during or after work-up of the hydrogenation in the different reactor.

* * * * *